(12) United States Patent
Cohen et al.

(10) Patent No.: US 11,648,113 B2
(45) Date of Patent: May 16, 2023

(54) GEAR DRIVE MECHANISM FOR HEART VALVE DELIVERY APPARATUS

(71) Applicant: Edwards Lifesciences Corporation, Irvine, CA (US)

(72) Inventors: Oren Cohen, Kadima (IL); Ofir Witzman, Kfar Saba (IL); Yair A. Neumann, Moshav Sede Varburg (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 200 days.

(21) Appl. No.: 17/063,428

(22) Filed: Oct. 5, 2020

(65) Prior Publication Data

US 2021/0015606 A1 Jan. 21, 2021

Related U.S. Application Data

(63) Continuation of application No. 16/105,353, filed on Aug. 20, 2018, now Pat. No. 10,806,573.

(60) Provisional application No. 62/548,855, filed on Aug. 22, 2017.

(51) Int. Cl.
*A61F 2/24* (2006.01)
*A61F 2/95* (2013.01)

(52) U.S. Cl.
CPC .......... *A61F 2/243* (2013.01); *A61F 2/2418* (2013.01); *A61F 2/2439* (2013.01); *A61F 2/9517* (2020.05); *A61F 2002/9511* (2013.01)

(58) Field of Classification Search
CPC .......... A61F 2/24; A61F 2/2418; A61F 2/243; A61F 2/2439; A61F 2/9517; A61F 2002/9511; A61B 17/00; A61B 17/34
See application file for complete search history.

(56) References Cited

U.S. PATENT DOCUMENTS

| | | |
|---|---|---|
| 519,297 A | 5/1894 | Bauer |
| 4,035,849 A | 7/1977 | Angell et al. |
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne |
| 5,176,698 A | 1/1993 | Burns et al. |
| 5,192,297 A | 3/1993 | Hull |
| 5,266,073 A | 11/1993 | Wall |
| 5,325,845 A | 7/1994 | Mair |
| 5,358,496 A | 10/1994 | Ortiz et al. |
| 5,411,552 A | 5/1995 | Andersen et al. |
| 5,554,185 A | 9/1996 | Block et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — George J Ulsh
(74) *Attorney, Agent, or Firm* — Klarquist Sparkman, LLP; Sean Seung Kyu Kim (57) ABSTRACT

A prosthetic valve delivery apparatus can comprise a handle, a gearbox, an input torque shaft and a plurality of output torque shafts. The input torque shaft can extend distally from the handle and can have a distal end portion operatively connected to the gearbox. The output torque shafts can be operatively connected to and extend distally from the gearbox. Rotation of the input torque shaft can cause rotation of the output torque shafts via the gear box.

20 Claims, 6 Drawing Sheets

(56) References Cited

U.S. PATENT DOCUMENTS

| | | |
|---|---|---|
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,414,916 B2 | 8/2016 | Costello et al. |
| 9,795,477 B2 | 10/2017 | Tran et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0089217 A1 | 4/2012 | Mews et al. |
| 2012/0123529 A1 | 5/2012 | Levi et al. |
| 2012/0172963 A1 | 7/2012 | Ryan et al. |
| 2012/0239142 A1 | 9/2012 | Liu et al. |
| 2013/0030519 A1 | 1/2013 | Tran et al. |
| 2013/0158655 A1 | 6/2013 | Sutton et al. |
| 2013/0317598 A1 | 11/2013 | Rowe et al. |
| 2014/0296962 A1 | 10/2014 | Cartledge et al. |
| 2017/0065415 A1 | 3/2017 | Rupp et al. |
| 2017/0128198 A1 | 5/2017 | Cartledge et al. |
| 2018/0153689 A1 | 6/2018 | Maimon et al. |
| 2018/0311473 A1* | 11/2018 | Laby ............... A61M 25/1036 |
| 2018/0344456 A1 | 12/2018 | Barash et al. |

FOREIGN PATENT DOCUMENTS

| | | |
|---|---|---|
| EP | 0592410 B1 | 10/1995 |
| EP | 0850607 A1 | 7/1998 |
| FR | 2815844 A1 | 5/2002 |

(56) References Cited

FOREIGN PATENT DOCUMENTS

| | | | |
|---|---|---|---|
| JP | 2004512080 | A | 4/2004 |
| JP | 2015500063 | A | 1/2015 |
| JP | 2016518223 | A | 6/2016 |
| WO | 9117720 | A1 | 11/1991 |
| WO | 9912483 | A1 | 3/1999 |
| WO | 0149213 | A2 | 7/2001 |
| WO | 0154625 | A1 | 8/2001 |
| WO | 0176510 | A2 | 10/2001 |
| WO | 0222054 | A1 | 3/2002 |
| WO | 0236048 | A1 | 5/2002 |
| WO | 0247575 | A2 | 6/2002 |
| WO | 02060352 | | 8/2002 |
| WO | 03030776 | A2 | 4/2003 |
| WO | 03047468 | A1 | 6/2003 |
| WO | 2004019825 | A1 | 3/2004 |
| WO | 2005084595 | A1 | 9/2005 |
| WO | 2006032051 | A2 | 3/2006 |
| WO | 2006111391 | A1 | 10/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | 2010121076 | A2 | 10/2010 |
| WO | 2013082583 | A1 | 6/2013 |
| WO | 2014186646 | A1 | 11/2014 |
| WO | 2017040823 | A1 | 3/2017 |

* cited by examiner

GEAR DRIVE MECHANISM FOR HEART VALVE DELIVERY APPARATUS

CROSS REFERENCE TO RELATED APPLICATION

This application is a continuation of U.S. application Ser. No. 16/105,353, filed Aug. 20, 2018, which claims the benefit of U.S. Provisional Application No. 62/548,855, filed Aug. 22, 2017, both of which are incorporated herein by reference.

FIELD

The present disclosure relates to implantable, mechanically expandable prosthetic devices, such as prosthetic heart valves, and to methods and delivery assemblies for, and including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Because of the drawbacks associated with conventional open-heart surgery, percutaneous and minimally-invasive surgical approaches are garnering attention. In one technique, a prosthetic device is configured to be implanted in a less invasive procedure by way of catheterization. For example, a collapsible transcatheter prosthetic heart valve can be crimped to a compressed state and percutaneously introduced in the compressed state on a catheter and expanded to a functional size at the desired position by mechanical expansion or using a self-expanding frame or stent. Despite the recent advancements in percutaneous valve technology, there remains a need for improved transcatheter heart valves and delivery devices for such valves.

SUMMARY

Embodiments of improved prosthetic implant delivery assemblies and frames therefor are disclosed herein, as well as related methods and devices for such assemblies. In several embodiments, the disclosed assemblies are configured for delivering replacement heart valves into a heart of a patient.

In one representative embodiment, a prosthetic valve delivery apparatus can comprise a handle, a gearbox, an input torque shaft, and a plurality of output torque shafts. The input torque shaft can extend distally from the handle and can have a distal end portion operatively connected to the gearbox. The output torque shafts can be operatively connected to and extend distally from the gearbox. Rotation of the input torque shaft can cause rotation of the output torque shafts via the gearbox.

In some embodiments, the prosthetic valve delivery apparatus can further comprise a motor disposed in the handle. The motor can be operatively connected to a proximal end portion of the input torque shaft. Actuation of the motor can result in rotation of the input torque shaft.

In some embodiments, the gearbox can comprise a drive gear and a plurality of driven gears. The drive gear can be operatively connected to and driven by the input torque shaft. The driven gears can be configured to be driven by the drive gear. Each driven gear can be operatively connected to and rotate one of the output torque shafts.

In some embodiments, the drive gear can comprise an internal gear and the driven gears can comprise pinion gears positioned inside of the internal gear.

In some embodiments, the drive gear can be mounted on the distal end portion of the input torque shaft and each driven gear can be mounted on one of the output torque shafts.

In some embodiments, the drive gear can have teeth that mesh with teeth of each driven gear.

In some embodiments, the gearbox can further comprise at least one idler gear configured to transfer rotational motion from the drive gear to one of the driven gears.

In some embodiments, the plurality of output torque shafts can comprise three output torque shafts.

In some embodiments, each output torque shaft can comprise a connector at its distal end configured to form a releasable connection with an actuator on a prosthetic heart valve.

In some embodiments, the input torque shaft can define a central rotation axis collinear with a central longitudinal axis of the delivery apparatus, and each output torque shaft can define a rotation axis offset from the central longitudinal axis of the delivery apparatus.

In some embodiments, the prosthetic heart valve delivery apparatus can be used in combination with a prosthetic valve comprising a radially expandable and compressible frame and a plurality of actuators configured to radially expand and compress the frame. Each output torque shaft can be releasably coupled to a screw of an actuator to transfer rotational motion from the torque shaft to the screw. Rotation of the screws can cause radial expansion or compression of the frame.

In some embodiments, the input torque shaft can extend at least the majority of the length of the delivery apparatus.

In another representative embodiment, a prosthetic valve delivery assembly can comprise a prosthetic valve and a delivery apparatus. The prosthetic valve can comprise a radially expandable and compressible frame and a plurality of actuators configured to radially expand and compress the frame. A delivery apparatus can comprise a handle, an input torque shaft extending from the handle, a gear mechanism coupled to a distal end portion of the input torque shaft, and a plurality of output torque shafts coupled to and extending distally from the gear mechanism. The gear mechanism can transfer rotational motion of the input torque shaft to the output torque shafts. Each output torque shaft can be releasably coupled to one of the actuators such that rotation of the output torque shafts causes the actuators to radially expand or compress the prosthetic valve.

In some embodiments, the distal end portion of the input torque shaft, the gear mechanism, and the output torque shafts can be configured to be inserted into a patient's vasculature.

In some embodiments, the gear mechanism can comprise a drive gear operatively connected to the distal end portion of the input torque shaft and a plurality of driven gears configured to be driven by the drive gear. Each driven gear can be operatively connected to one of the output torque shafts.

In another representative embodiment, a method of implanting a prosthetic heart valve can comprise inserting a prosthetic heart valve and a distal end portion of a delivery apparatus into a patient's vasculature and rotating the input torque shaft. The prosthetic heart valve can be in a radially compressed state and the delivery apparatus can comprise an input torque shaft, a gear mechanism coupled to the input torque shaft along the distal end portion of the delivery apparatus inserted into the patient's vasculature, and a plurality of output torque shafts releasably coupled to actuators on the prosthetic heart valve. Rotation of the input torque shaft can produce rotation of the output torque shafts via the gear mechanism. Rotation of the output torque shafts can actuate the actuators, which can cause the prosthetic heart valve to expand from the radially compressed state to a radially expanded state.

In some embodiments, the act of inserting the prosthetic heart valve and the distal end portion of the delivery apparatus into the patient's vasculature can comprise advancing the prosthetic heart valve and the distal end portion of the delivery apparatus through the aorta such that the input torque shaft extends through the aortic arch, and the output torque shafts and the gear mechanism are located in the ascending aorta.

In some embodiments, the method of implanting the prosthetic heart valve can further comprise releasing the output torque shafts from the actuators.

In some embodiments, the output torque shafts can be rotated at a different rotational speed than the input torque shaft.

In some embodiments, at least one of the output torque shafts can rotate in a different direction than the input torque shaft.

In some embodiments, the gear mechanism can comprise a drive gear operatively connected to the distal end portion of the input torque shaft and a plurality of driven gears configured to be driven by the drive gear. Each driven gear can be operatively connected to one of the output torque shafts.

The foregoing and other objects, features, and advantages of the invention will become more apparent from the following detailed description, which proceeds with reference to the accompanying figures.

DETAILED DESCRIPTION

Described herein are examples of prosthetic implant delivery assemblies and components thereof which can improve a physician's ability to control the size of a mechanically-expandable prosthetic implant, such as prosthetic valves (e.g., prosthetic heart valves or venous valves), stents, or grafts, as well as facilitate separation of the prosthetic implant from the delivery assembly, during the implantation procedure. The present disclosure also discloses frames for use with such prosthetic implants.

Figure 1:
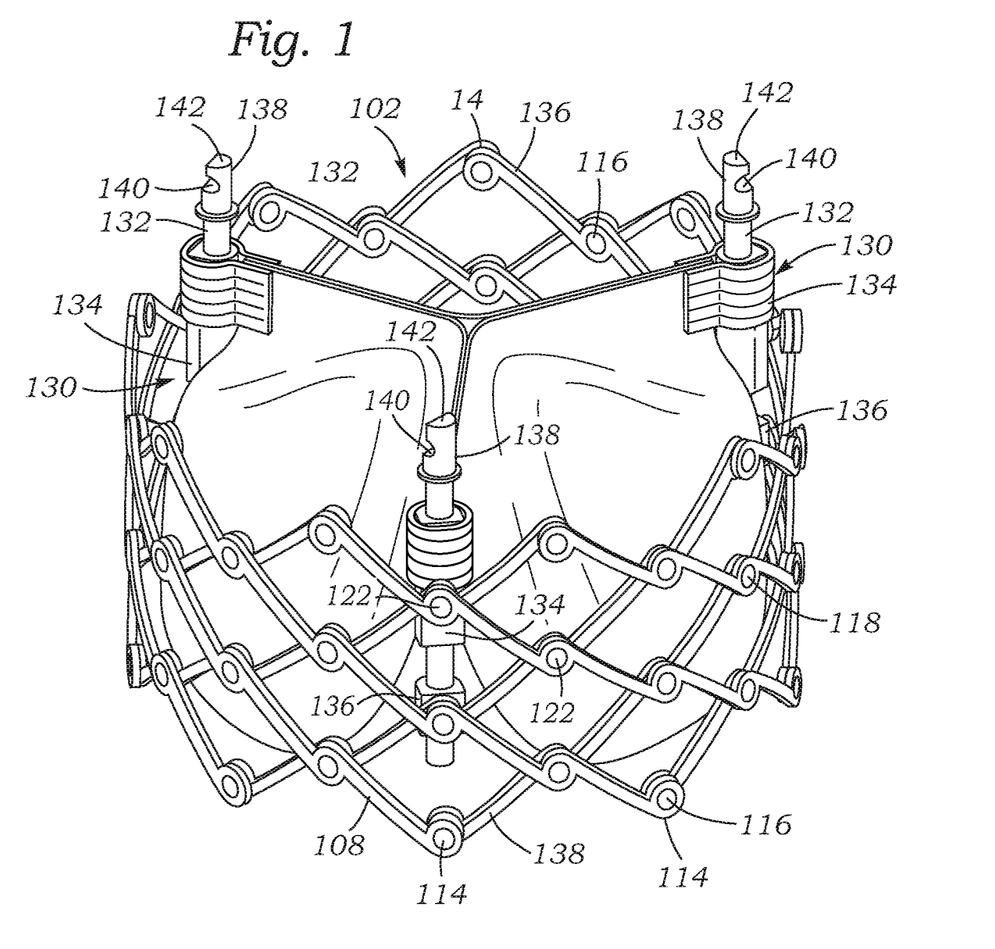
FIG. 1 is a perspective view of an exemplary embodiment of a prosthetic heart valve.

FIG. 1 shows an exemplary prosthetic heart valve 100. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve 100 can also be adapted to be implanted in other tubular organs or passageways in the body. The prosthetic valve 100 can comprise a stent or frame 102, a valvular structure 110, and inner and/or outer sealing means. The prosthetic valve 100 can comprise an inflow end portion 104 and an outflow end portion 106.

In the illustrated embodiment, the sealing means comprises an outer skirt (not shown in FIG. 1), which can be secured to the outer surface of the frame 102 with sutures, an adhesive, and/or other suitable techniques or mechanisms. The outer skirt can help establish a seal with the native tissue at the implantation site to prevent or minimize perivalvular leakage. In alternative embodiments, the prosthetic valve 100 can have a skirt or sealing member mounted on the inside of the frame 102 or a skirt or sealing member mounted on the inside and outside of the frame 102. The skirt can be formed from natural tissue (e.g., pericardial tissue) or any of various biocompatible synthetic materials, including biocompatible fabrics (e.g., polyethylene terephthalate (PET) fabric).

The valvular structure 110 can comprise three leaflets 112, collectively forming a leaflet structure, which can be arranged to collapse in a tricuspid arrangement. The lower edge of leaflet structure 110 desirably has an undulating, curved scalloped shape. By forming the leaflets with this scalloped geometry, stresses on the leaflets are reduced, which in turn improves durability of the prosthetic valve. Moreover, by virtue of the scalloped shape, folds and ripples at the belly of each leaflet 112 (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end 104 of the prosthetic valve 100. The leaflets 112 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein in its entirety.

Figures 2, 3:
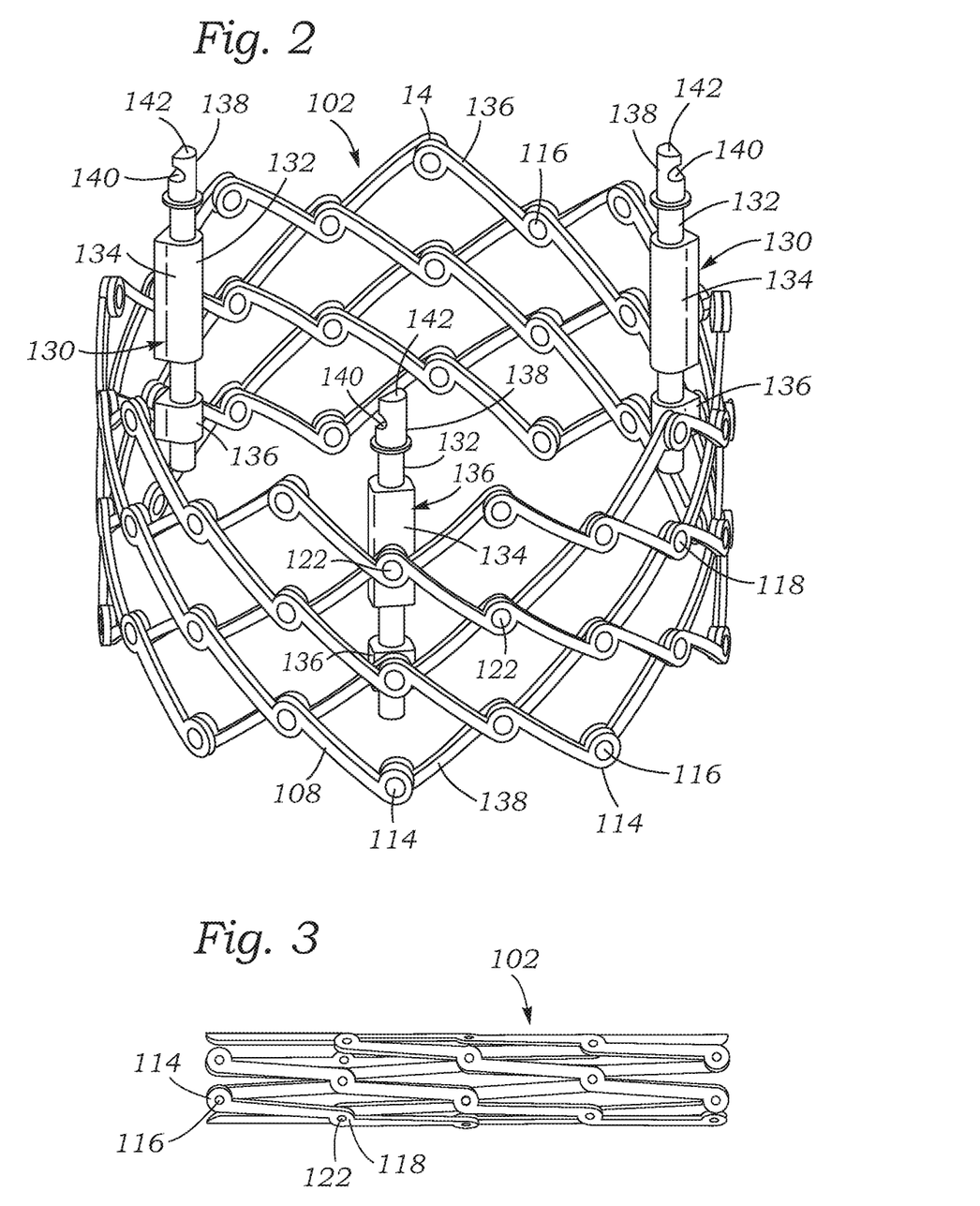
FIG. 2 is a perspective view of an exemplary frame of the prosthetic heart valve of FIG. 1 in a radially expanded configuration.
FIG. 3 shows the frame of FIG. 2 in a radially collapsed configuration.

The prosthetic valve 100 can define a longitudinal axis extending through the inflow end portion 104 and the outflow end portion 106. The prosthetic valve 100 can also comprise one or more actuators 130, including sleeves 134, configured to radially expand and compress the frame 102, as discussed more fully below in connection with FIG. 2. In the illustrated embodiment, the prosthetic valve 100 includes three such actuators 130, although a greater or fewer number of actuators could be used in other embodiments. The leaflets 112 can have commissure attachments that wrap around the sleeves 134 of the actuators 130. FIG. 2 shows the frame 102 of FIG. 1 including the actuators 130 without the valvular structure 110 or the outer skirt for purposes of illustration. The frame 102 can be made of any of various suitable materials, such as stainless steel or a nickel titanium alloy ("NiTi"), for example Nitinol. The frame 102 can include a plurality of interconnected lattice struts 108 arranged in a lattice-type pattern and forming a plurality of apices 114 at an outflow end 124 of the frame 102. The struts 108 can also form similar apices 114 at an inflow end 126 of the frame 102. The lattice struts 108 are shown as positioned diagonally, or offset at an angle relative to, and radially offset from, the longitudinal axis of the prosthetic valve 100. In other implementations, the lattice struts 108 can be offset by a different amount than depicted in FIG. 2, or some or all of the lattice struts 108 can be positioned parallel to the longitudinal axis of the prosthetic valve 100.

The lattice struts 108 can be pivotably coupled to one another. In the illustrated embodiment, for example, the end portions of the struts 108 forming the apices 114 at the outflow end 124 and at the inflow end 126 of the frame 102 can have a respective opening or aperture 116. The struts 108 also can be formed with openings or apertures 118 spaced apart along their lengths between the opposite ends of the struts. Respective hinges can be formed at the apices 114 and at the junctions/locations where struts 108 overlap each other between the ends of the frame via fasteners 122, which can comprise rivets or pins that extend through the apertures 116, 118. The hinges can allow the struts 108 to pivot relative to one another as the frame 102 is expanded or contracted, such as during assembly, preparation, or implantation of the prosthetic valve 100. For example, the frame 102 (and thus the prosthetic valve 100) can be manipulated into a radially compressed or contracted configuration (see, e.g., FIG. 3) and inserted into a patient for implantation. Once inside the body, the prosthetic valve 100 can be manipulated into an expanded state (e.g., FIG. 2) and then released from the delivery apparatus, as further described below.

The frame 102 can be formed using any suitable technique. Suitable techniques can include separately forming individual components (e.g., the struts 108 and fasteners 122) of the frame and then mechanically assembling and connecting the individual components to form the frame 102. The struts 108 and fasteners 122 can be formed, for example, by laser cutting those components from sheets or tubes of metal, or by electroforming (electroplating or electrodeposition) or physical vapor deposition. In some embodiments, electroforming or physical vapor deposition can be used to form subcomponents of the frame 102 or the entire frame 102 with pivotable connections between the struts 108. In one implementation, for example, electroforming or physical vapor deposition can be used to form struts 108 having integral fasteners 122. The individual struts 108 can be assembled together into a frame by inserting the integral fasteners 122 of each strut through a corresponding aperture of an adjacent strut. In some embodiments, electroforming or physical vapor deposition can be used to form the entire frame 102 in its final, cylindrical shape. In other embodiments, electroforming or physical vapor deposition can be used to form the entire frame in a flattened configuration, after which the ends of the flattened frame are connected to each other to form the final cylindrical shape of the frame.

In other embodiments, the lattice struts 108 are not coupled to each other with respective hinges (e.g., fasteners 122) but are otherwise pivotable or bendable relative to each other to permit radial expansion and contraction of the frame 102. For example, the frame 102 can be formed (e.g., via laser cutting, electroforming or physical vapor deposition) from a single piece of material (e.g., a metal tube). Further details regarding the construction of the frame 102 are disclosed in U.S. Patent Publication No. 2018/0153689 and U.S. application Ser. No. 15/995,528, filed Jun. 1, 2018, which are incorporated herein by reference in their entirety.

Further details regarding transcatheter prosthetic heart valves, including the manner in which the valvular structure 110 can be coupled to the frame 102 of the prosthetic valve 100, can be found, for example, in U.S. Pat. Nos. 6,730,118, 7,393,360, 7,510,575, 7,993,394, and 8,652,202, and U.S. application Ser. No. 15/978,459, filed May 14, 2018, which are incorporated herein by reference in their entireties.

Each of the actuators 130 can comprise a screw or threaded rod 132, a first anchor member in the form of a sleeve or cylinder 134, and a second anchor member in the form of a threaded nut 136. The rod 132 extends through the sleeve 134 and the nut 136. The sleeve 134 can be secured to frame 102, such as with one of the fasteners 122 that forms a hinge at the junction of two struts 108. The nut 136 can be secured to the frame 102 at a location axially spaced from the attachment location of the sleeve 134, such as with one of the fasteners 122 at a junction between two struts 108. Each actuator 130 is configured to increase the distance between the attachment locations of a respective sleeve 134 and nut 136, which causes the frame 102 to elongate axially and compress radially, and to decrease the distance between the attachment locations of a respective sleeve 134 and nut 136, which causes the frame 102 to foreshorten axially and expand radially.

For example, the lower end portion of each screw 132 (the portion extending through the nut 136) can have external threads that engage internal threads of the nut 136 while the upper portion of the screw 132 (the portion extending through the sleeve 134) can be fixed axially relative to the sleeve 134 but free to rotate relative to the sleeve 134. In this manner, rotation of the screw 132 in a first direction causes the nut 136 to travel axially along the screw in a direction away from the sleeve 134 to radially compress the frame (with the nut applying a distally directed force to the frame), while rotation of the screw in a second direction causes the nut 136 to travel axially along the screw in a direction toward the sleeve 134 to radially expand the frame (with the nut applying a proximally directed force to the frame).

In another embodiment, the screw 132 of each actuator 130 can have external threads along its upper portion to engage internal threads of a corresponding sleeve 134, while the lower portion of the screw 132 can be fixed axially relative to an anchor member 136 but free to rotate relative to the anchor member 136. In this embodiment, the anchor member 136 need not have internal threads, thus is not referred to as a "nut". Rotation of the screw 132 in this example causes the sleeve 134 to move toward or away from the anchor member 136 to radially expand or compress the frame, depending on the rotational direction of the screw.

In another embodiment, the screw 132 of each actuator can have external threads along its upper and lower portion to engage internal threads of the sleeve 134 and the nut 136. The internal threads of the sleeve 134 and the nut 136 are threaded in the opposite direction. In this manner, rotation of the screw 132 in a first direction causes both the sleeve 134 and the nut 136 to travel along the length of the screw towards each other to radially expand the frame. Rotation of the screw 132 in a second direction causes both the sleeve 134 and the nut 136 to travel along the length of the screw away from each other to radially compress the frame.

Each screw 132 can include an attachment member 138 along a proximal end portion of the screw configured to form a releasable connection with a corresponding drive shaft of a delivery apparatus to transfer torque of the delivery apparatus to the screw. The attachment member 138 in the illustrated configuration comprises a notch 140 and a projection 142 that can engage a corresponding projection of a drive shaft of the delivery apparatus, as described in further detail below.

When expanding the frame 102 from a radially compressed state to a radially expanded state, it is desirable to rotate the screws 132 in a synchronized fashion. Additionally, a proper amount of torque must be transferred from the handle of a delivery system to the screws 132. In some embodiments, torque can be transmitted directly from the handle of the delivery apparatus to each of the screws 132 via separate drive shafts that extend nearly the entire length of the delivery apparatus from the handle to the prosthetic valve coupled to the distal end of the delivery apparatus. This arrangement requires that torque to each screw 132 be transmitted via a relatively long drive shaft having a relatively small diameter. As shown in the formulas below, the amount of torque that can be transmitted along the length of a shaft is inversely proportional to the length of a shaft and directly proportional to the diameter of a shaft.

For a solid shaft having a circular cross-section:

$$T = \frac{D^4 \pi G \theta}{32L};$$

and
for a tubular shaft:

$$T = \frac{(OD^4 - ID^4)\pi G \theta}{32L};$$

where T=torque; D=diameter; G=shear modulus; L=shaft length; OD=tube outer diameter; and ID=tube inner diameter. Also, deflection of the delivery apparatus as it is being advanced through the patient's vasculature can cause one or more of the draft shafts to elongate and one or more of the drive shafts to foreshorten, which can adversely affect the ability of the drive shafts to achieve synchronized rotation of the actuators at the desired torque. Therefore, it can be advantageous to have a mechanism along the distal end of the delivery system adjacent to the prosthetic valve to actuate the actuators 130. This can enable the use of one robust torque shaft for transmitting torque from the handle along the majority of the length of the delivery apparatus rather than multiple smaller shafts. This can also allow the lengths of the individual drive shafts that actually transmit torque directly to the actuators to be minimized, which promotes the application of torque to the actuators and avoids elongation and foreshortening of the drive shafts.

Figure 4:
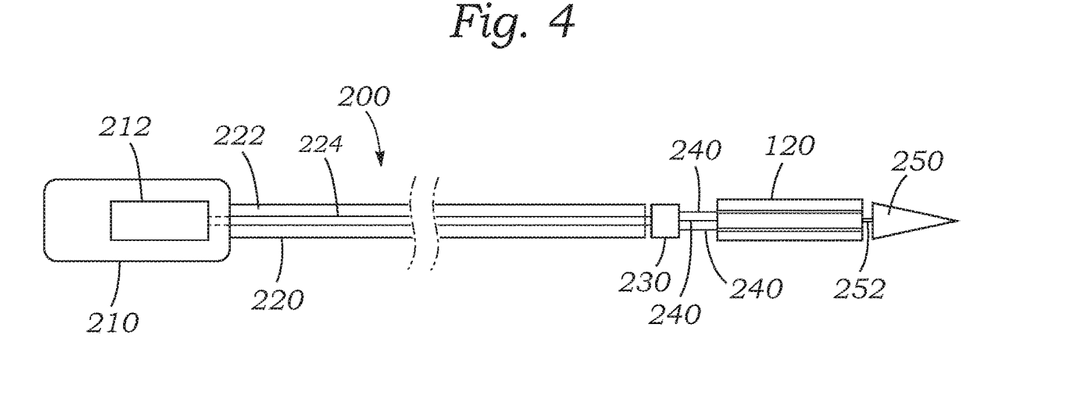
FIG. 4 shows an exemplary prosthetic valve delivery apparatus that can be used for implanting the prosthetic heart valve of FIG. 1.

FIG. 4 shows an exemplary embodiment of a prosthetic valve delivery apparatus 200 that can be used for percutaneously delivering and implanting a prosthetic heart valve, such as prosthetic heart valve 100, in the heart of a patient. The delivery apparatus 200 of FIG. 4 comprises a handle 210, an outer shaft or catheter 220 extending distally from the handle 210, an input torque shaft 224 extending distally from the handle 210 through the outer shaft 220, a gearbox, or gear mechanism, 230 operatively connected to a distal end portion of the input torque shaft 224, a plurality of output torque shafts 240, and a nose cone 250. The nose cone 250 can be mounted on the distal end portion of an innermost shaft 252 that serves as a guidewire lumen, which can extend coaxially through the input torque shaft 224 and can have a proximal end portion coupled to the handle 210.

The outer catheter 220 can be a steerable catheter, which can be steered by a user as it is advanced through the patient's vasculature by adjusting the curvature of the outer catheter 220. In particular embodiments, the delivery apparatus can have one or more pull wires extending through the outer catheter with proximal end portions of the pull wires coupled to an adjustment knob on the handle 210. The adjustment knob is configured to vary the tension in the one or more pull wires, which is effective to vary the curvature of the outer catheter 220 and the shaft 224. Further details regarding a steering mechanism for controlling the curvature of a delivery apparatus are disclosed in U.S. Patent Publication No. 2016/0158497, which is incorporated herein by reference.

Each output torque shaft 240 can have a proximal end portion connected to the gearbox 230 and a distal end portion releasably connected to a respective screw 132 of an actuator 130, as further discussed below. Each output torque shaft 240 can comprise, for example, a rod, a rigid tube, a cable, a laser cut tube, a hypotube, or any other elongated annular structure (e.g., any tubular or cylindrical structure). A proximal end portion of the input torque shaft 224 can be operatively connected to an actuator, such as a motor 212, housed within or coupled to the handle 210. The motor 212 can be, for example, an electric motor powered by batteries, which can also be housed within the handle 210. In alternative embodiments, the motor 212 can be a hydraulically driven or a pneumatically driven motor. The motor 212 is operable to actuate or rotate the input torque shaft 224, which in turn actuates or rotates the output torque shafts 240 via the gearbox 230, which in turn rotate the screws 132 to radially expand and compress the prosthetic valve, as explained in further detail below. Further details regarding a motorized handle that can be used to apply torque to the torque shaft 224 is disclosed in U.S. Patent Publication No. 2014/0296962, which is incorporated herein by reference. The input torque shaft 224 spans the majority of the delivery apparatus and can have a larger diameter than in delivery systems where multiple torque shafts extend all the way from the handle to the prosthetic valve.

The delivery apparatus 200 can have various user interface controls to control the operation of the delivery apparatus. For example, referring to FIG. 4A, the handle 210 can have one or more buttons 280a, 280b that control operation of the motor 212. The button 280a can be operable to produce rotation of the torque shaft 224 in a first direction to radially expand the prosthetic valve 100. The button 280b can be operable to produce rotation of the torque shaft 224 in a second direction, opposite the first direction, to radially compress the prosthetic valve 100.

Figure 4A:
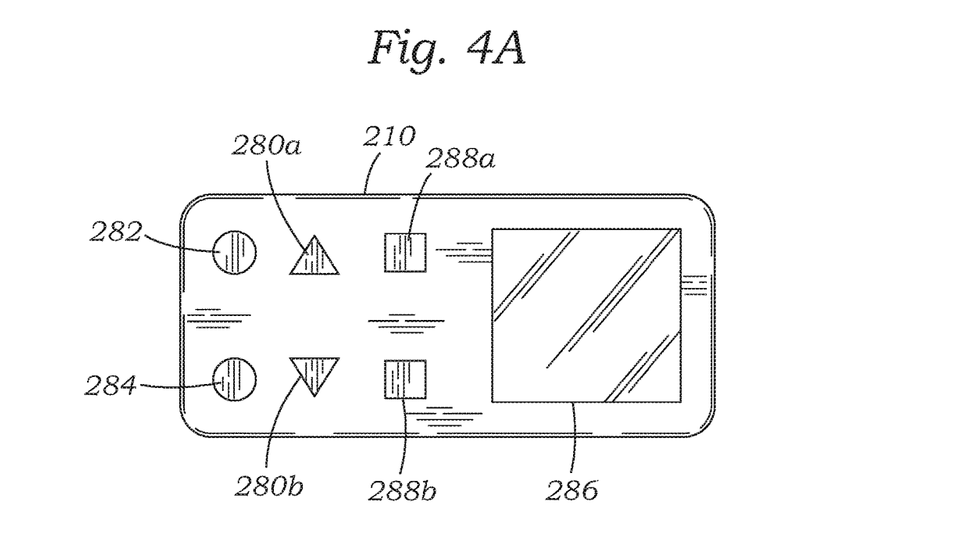
FIG. 4A is a top plan view of an exemplary embodiment of a handle for a delivery apparatus.

The handle 210 can also include a processor and memory for storing and executing software that can control deployment of the prosthetic valve. For example, in lieu of or in addition to the buttons 280a, 280b, a button 282 can be provided to control operation of the motor. In one implementation, the button 282 can be operable to actuate the motor 212 when pressed by a user, which can begin a deployment procedure whereby the prosthetic valve is automatically expanded according to a predetermined algorithm. For example, the prosthetic valve can be expanded in a pulsed or stepped manner, as disclosed in U.S. U.S. Patent Publication No. 2014/0296962. The handle 210 can also include a stop button 284 that is operable to stop or discontinue expansion of the prosthetic valve at any time during the expansion process. The handle 210 can also include a visual display 286, which can display text, graphics and/or other information regarding the deployment of the prosthetic valve.

The delivery apparatus can further include another motor (which can be housed in the handle 210) and additional buttons 288a, 288b (e.g., on the handle) for controlling the curvature of the outer catheter 220 and the shaft 224. For example, the button 288a can be operable to produce rotation of the motor in a first direction to tension the one or more pull wires and cause the outer catheter 220 to bend or curve, such as when navigating around the aortic arch. The button 288b can be operable to produce rotation of the motor in a second direction, opposite the first direction, to reduce tension in the one or more pull wires, allowing the outer catheter to straighten.

The buttons 280a, 280b, 282, 284, 288a, 288b can be any of various shapes and sizes. Also, any of various switches or dials can be provided to perform any of the functions described above. For example, a three-position switch can replace buttons 280a, 280b. The switch can be moved between a first position that rotates the motor 212 in the first direction to expand the prosthetic valve, a second, neutral position in which the motor 212 is de-activated, and a third position that rotates the motor 212 in the second direction to compress the prosthetic valve. In alternative embodiments, the display 286 can be a touch screen with a user interface and any of the buttons 280a, 280b, 282, 284, 288a, 288b can be replaced with buttons on the touch screen display.

In some embodiments, the handle 210 can be in communication with a separate control unit (via a wireless or wired communication link) that includes a display and/or a processor for executing software, in which case the handle 210 need not include those features.

In alternative embodiments, the delivery apparatus need not include a motor to rotate the input torque shaft 224 and instead the input torque shaft 224 can be manually rotated by the user. For example, the proximal end portion of the torque shaft 224 can be connected to a rotatable knob or wheel mounted on the handle that is operable to rotate the torque shaft 224 when the knob or wheel is rotated by the user.

Figure 5:
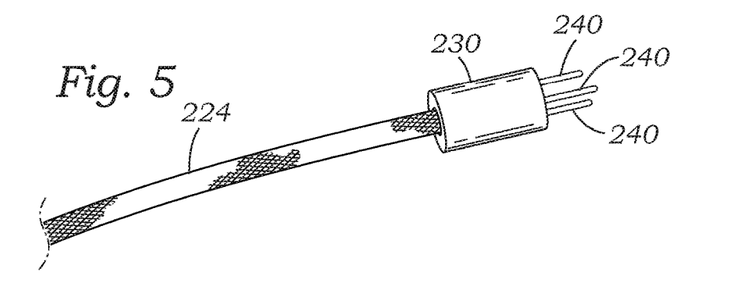
FIG. 5 is a perspective view of an input torque shaft, gearbox, and output torque shafts of the prosthetic valve delivery apparatus of FIG. 4.

FIG. 5 shows perspective view of the distal end portion of the input torque shaft 224, the gearbox 230, and the output torque shafts 240. For purposes of illustration, the outer catheter 220 is omitted from FIG. 5. The input torque shaft 224 can comprise a robust torque transmitting cable connected to the handle 210 at its proximal end and connected to the gearbox 230 at its distal end. The gearbox 230 can transfer the torque from the input torque shaft 224 to each of the output torque shafts 240. The gearbox 230 can also be configured to reduce or increase the rotation speed and/or the torque of the input torque shaft 224 so as to rotate the output torque shafts 240 at a different rotation speed and/or toque than the input torque shaft as desired.

Figure 6:
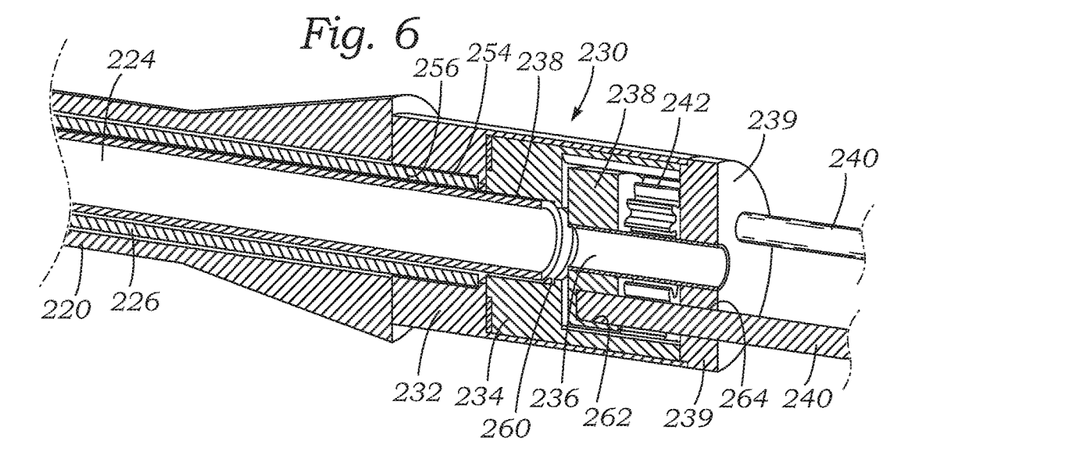
FIG. 6 is a cross-sectional view of the input torque shaft, gearbox and output torque shafts shown in FIG. 5.
Figure 7:
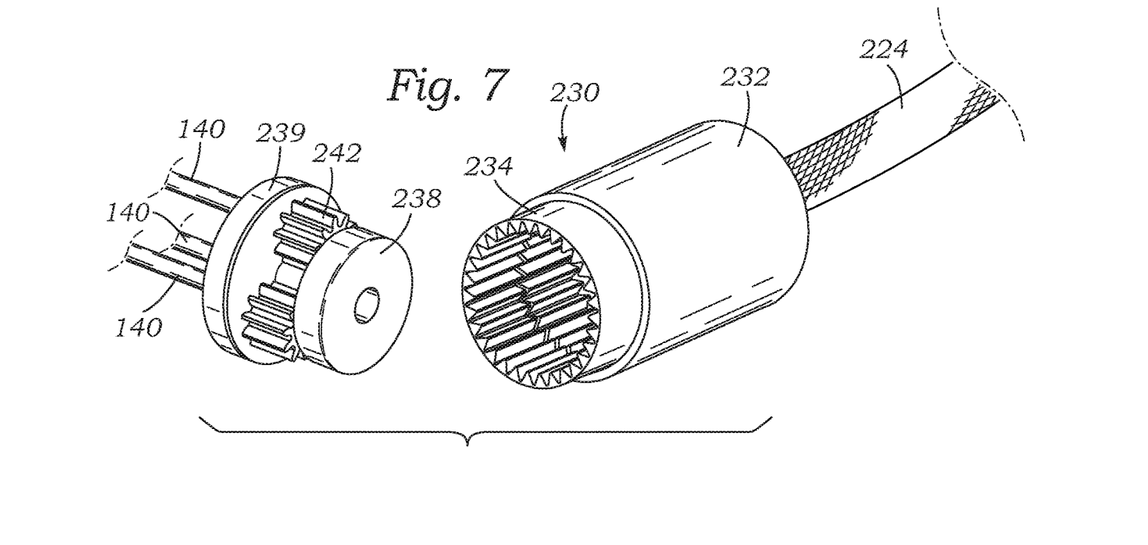
FIG. 7 is an exploded, perspective view of the gear box of FIGS. 4-6.

FIG. 6 shows an internal cross-sectional view of the gearbox 230 and the distal end portion of the input torque shaft 224. FIG. 7 shows a perspective view of the gearbox 230 in a disassembled state. Referring to FIGS. 6 and 7, the input torque shaft 224 can be housed within a static (non-rotatable) flex shaft 226, which extends through the lumen of the outer shaft 220. The static flex shaft 226 can have a proximal end portion connected to the handle 210 and a distal end portion 254 that can extend axially beyond the outer shaft 220 into a proximal opening 256 of a gearbox housing 232. The distal end portion 254 can be secured inside the opening of the gearbox housing 232, such as with an adhesive, friction fit, fasteners, welding, and/or other suitable techniques or mechanisms, so as to secure the gearbox relative to the outer shaft 220 and the flex shaft 226

The gearbox 230 defines a gear train comprising a drive gear and a plurality of driven gears for transferring rotational motion of the input torque shaft to each output torque shaft. In the illustrated embodiment, a distal end portion 258 of the input torque shaft 224 can extend axially beyond the distal end of the flex shaft 226 where it is connected to a drive gear 234, which in turn is connected to a plurality of driven gears 242. Each of the driven gears 242 is connected to and rotates a respective output torque shaft 240. In the illustrated embodiment, the distal end portion 258 of the input torque shaft 224 extends into a central opening 260 of the drive gear 234, which can comprise an internal gear having teeth on an inner surface of the gear. The distal end portion 258 can be secured inside of the central opening 260, such as with an adhesive, friction fit, fasteners, welding, and/or other suitable techniques or mechanisms. The driven gears 242 can be pinion gears having external teeth that mesh with the teeth of the drive gear 234.

The gearbox 230 in the illustrated configuration further comprises a proximal plate 238 housed within the drive gear 234, a distal plate 239 mounted to the distal end of the housing 232, and an inner shaft or tubular portion 236 that extends from the proximal plate 238 to the distal plate 239. The tubular portion 236 can be fixed to the proximal and distal plates 238, 239 so as to keep them properly spaced from and parallel to each other. The tubular portion 236 provides a lumen for allowing the innermost shaft 252 (FIG. 4) to extend through the gearbox 230 without interfering with the gears 234, 242. A guidewire (not shown), as typically known in the art, can extend through the innermost shaft 252 and can be used to guide the delivery apparatus 200 through a patient's vasculature. Each output torque shaft 240 can be secured within an opening of a respective gear 242, such as with an adhesive, friction fit, welding, and/or other suitable techniques or mechanisms. The output torque shafts 240 can freely rotate with respect to the proximal and distal plates 238, 239 while remaining perpendicular to the proximal and distal plates 238, 239.

Each output torque shaft 240 can have a proximal end portion supported within a respective opening 262 in the proximal plate 238 and an intermediate portion supported within a respective opening 264 in the distal plate 239. The output torque shafts 240 can rotate within their corresponding openings 262, 264 within the proximal and distal plates 238, 239, which help retain proper alignment of the driven gears 242 within the drive gear 234. Each output torque shaft 240 has a distal end portion releasably connected to a respective screw 132 of an actuator 130, as further described below.

Figure 8A:
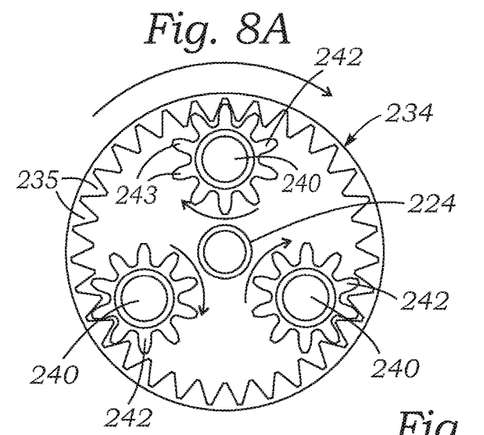
FIGS. 8A-8B are end views of the gearbox of FIGS. 5-6 showing the operation of the gears inside of the gearbox.
Figure 8B:
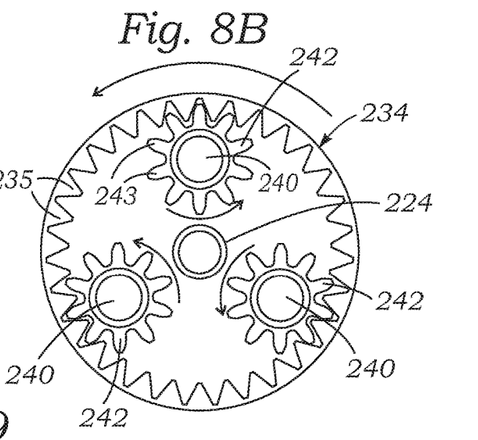

When the input torque shaft 224 is actuated by the motor 212, the input torque shaft 224 rotates, which causes the drive gear 234 to rotate. The rotation of the drive gear 234 in turn causes the driven gears 242 to rotate as shown in more detail in FIGS. 8-9. Each driven gear 242 in turn rotates an output torque shaft 240, which in turn rotates a respective screw 132 of an actuator to effect radial expansion and compression of the frame 102 of the prosthetic valve. In one specific embodiment, the internal gear 234 can have 31 teeth, a module of 0.2, a pressure angle of 20°, and a backlash of 0.1 mm. In other embodiments, the internal gear 234 can have any other parameters. The number of pinions 242 in the gearbox 230 can be equal to the number of output torque shafts 240. Each pinion 242 can have 10 teeth, a module of 0.2, a pressure angle of 20°, and a backlash of 0.1 mm. In other embodiments, the internal gear 234 and the pinions 242 can have various other parameters, depending on the particular application.

FIGS. 8A and 8B further illustrate the operation of the gearbox 230. The internal gear 234 can have a plurality of teeth 235 that can engage respective teeth 243 of the pinions 242. As shown in FIG. 8A, clockwise rotation of the internal gear 234 results in corresponding clockwise rotation of the pinions 242. As shown in FIG. 8B, counter-clockwise rotation of the internal gear 234 results in corresponding counter-clockwise rotation of the pinions 242. The pinions 242 can be connected to respective output torque shafts 240 such that rotation of the pinions 242 causes corresponding rotation of the output torque shafts 240 in the same direction. As such, the gearbox 230 can convert a single input torque from the input torque shaft 224 into a number of output torques equal to the number of output torque shafts 240 connected to the gearbox 230. The gearbox 230 can also shift the rotation axis from the center axis of the input torque shaft 224 (which is collinear to the central longitudinal axis of the delivery apparatus) to the rotation axes of the output torque shafts 240, which are offset from the longitudinal axis of the delivery apparatus. Shifting the axes of rotation is advantageous because the screws 132 of the actuators 130 are also offset from the central longitudinal axis of the frame 102.

In the illustrated embodiment, the gear ratio of the drive gear to the driven gears is greater than 1 (e.g., a gear ratio of 3.1:1 for an internal gear having 31 teeth and pinions having 10 teeth), so that the output torque shafts 240 rotate faster than the input torque shaft 224. In alternative embodiments, the gearbox can be configured to have a gear ratio of the drive gear to the driven gears that is less than 1 such that the output torque shafts rotate slower than the input torque shaft.

Figure 9:
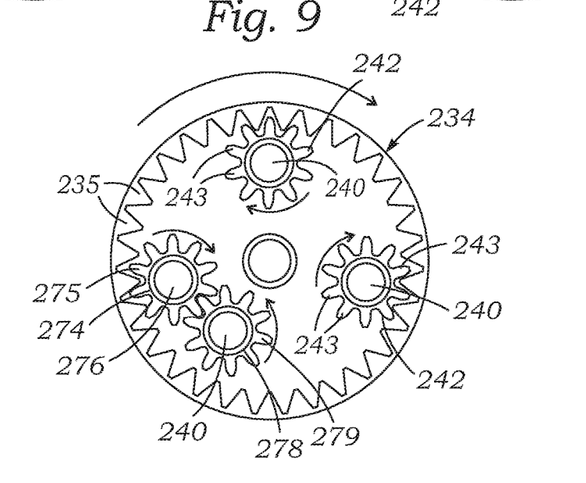
FIG. 9 is an end view showing the inside of an alternative embodiment of a gearbox.

FIG. 9 shows an alternative embodiment of a gearbox. The gearbox of FIG. 9 is similar to the arrangement shown in FIGS. 8A-8B, except that one or more idler gears can be added to change the direction of rotation from the internal gear 234 to one or more of the driven pinion gears 242. In the illustrated embodiment, two driven pinion gears 242 mounted on respective output torque shafts 240 have teeth 243 that engage the internal teeth 235 of the gear 234 as previously described. An idler pinion gear 274 can be mounted on a respective shaft 276 within the internal gear 234 and can have teeth 275 that mesh with the teeth 235 of the internal gear 234. A third driven pinion gear 279, mounted on one of the output torque shafts 240, has teeth 279 that mesh with the teeth of the idler pinion gear 274. Thus, in use, rotation of the internal gear 234 causes rotation of the pinion gears 242 and their respective output shafts 240 in the same direction, and rotation of the pinion gear 278 and its respective output shaft 240 in the opposite direction (through the idler gear). Such a configuration can be advantageous if one or more of the screws 132 of the actuators 130 are threaded in a different direction from the other screws (e.g., one or more screws 132 are right-hand screws while one or more are left-hand screws). In alternative embodiments, the gearbox can have more than one idler gear, such as two idler gears to change the direction of rotation of two of the driven pinion gears, or three idler gears to change the direction of rotation of all three driven pinion gears.

Figure 10:
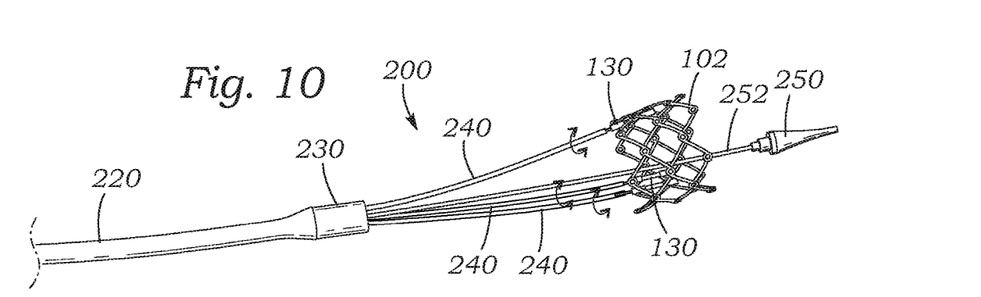
FIG. 10 is a perspective view of the distal end portion of the delivery apparatus and the prosthetic valve shown in FIG. 1, showing the prosthetic valve in a radially expanded state.
Figure 11:
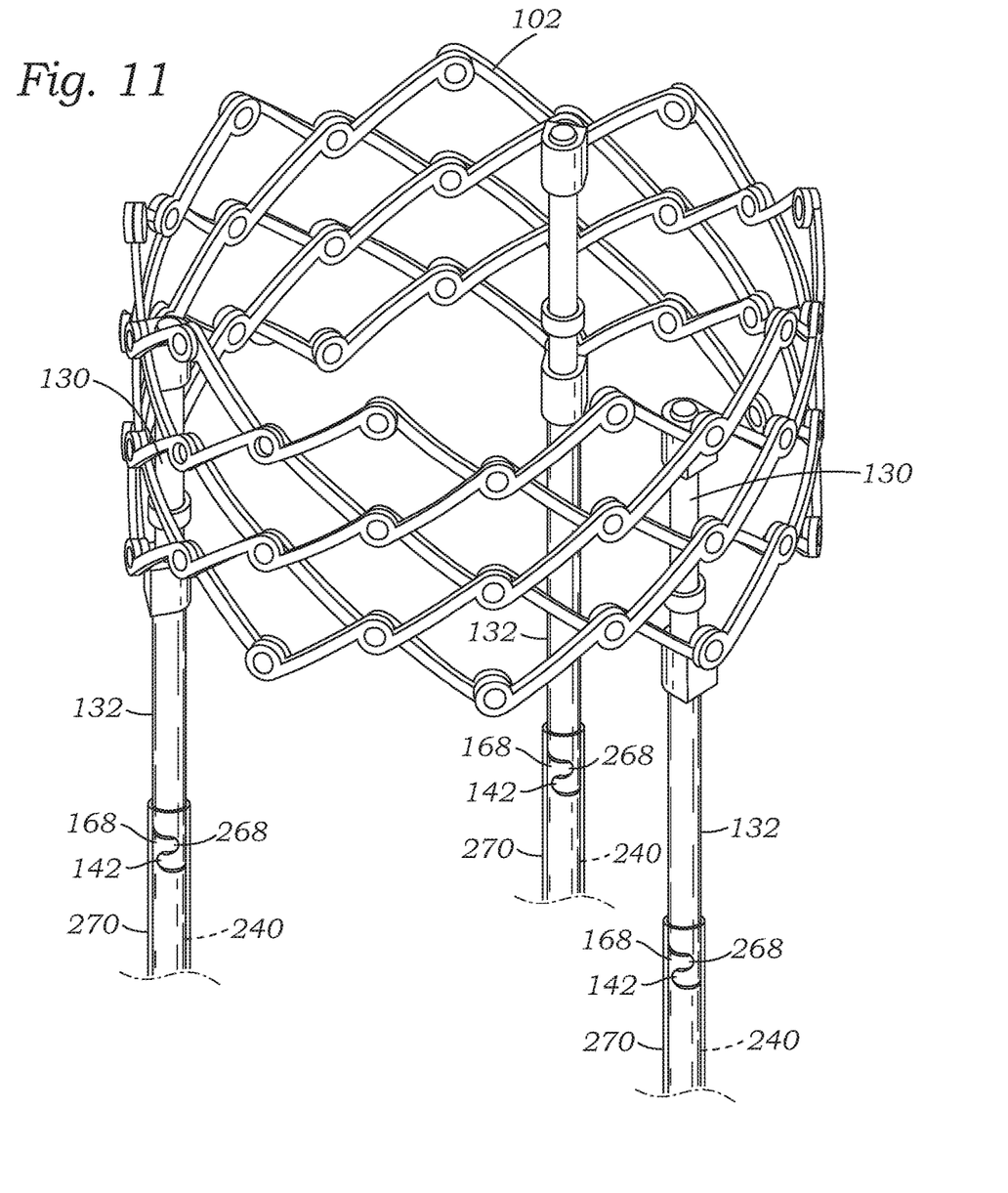
FIG. 11 is an enlarged, perspective view showing the prosthetic valve of FIG. 10 and the distal end portions of the output torque shafts releasably coupled to the actuators of the prosthetic valve.

FIGS. 10 and 11 shows the distal end portion of the delivery apparatus 200 releasably connected to the frame 102 of the prosthetic valve 100. As shown, each output torque shaft 240 can have a distal end portion 266 configured to mate with a corresponding attachment member 138 of a screw 132 of an actuator 130. In the illustrated embodiment, for example, the distal end portion 266 can be formed with a projection 268 shaped to be received in a notch 140 of an attachment member 138 and a notch shaped to receive a projection 142 of an attachment member 138. A sleeve 270 can extend over the distal end portion 266 of each output shaft 240 and a mating attachment member 138 of a screw 132 to maintain the connection between the output shaft 240 and the screw 132. Each sleeve 270 can extend proximally from the prosthetic valve to the delivery apparatus and is configured to be moved in the longitudinal direction to uncover the mating connection between the attachment member 138 and the distal end portion 266 of an output shaft. In particular embodiments, for example, each sleeve 270 can be connected to a wire or shaft that can be manipulated by a user to produce proximal movement of the sleeve 270 relative to the associated shaft 240. When the sleeves 270 are retracted proximally to uncover the connection between the screws 132 and the shafts 240, the shafts 240 can release/de-couple from the screws 132 by retracting or pulling the shafts 240 slightly relative to the screws 132.

Other configurations and devices for forming a releasable connection between a drive shaft of a delivery apparatus and a rotatable screw of a prosthetic valve frame, such as those described in U.S. Patent Application Publication 2014/0296962, can be used to form a releasable connection between each torque shaft 240 and screw 132.

To use the delivery apparatus 200 to deliver and implant the prosthetic valve 100 at a desired location within the heart (e.g., the native aortic valve), the prosthetic valve 100 can first be radially compressed or crimped to a compressed state, as shown in FIG. 3. Alternatively, the prosthetic valve 100 can begin in a radially expanded state as shown in FIG. 2. The distal end portions 266 of the output torque shafts 240 can be connected to the attachment members 138 of the screws 132 and the sleeves 270 can be placed over the distal end portions 266 and the attachment members 138.

Once the output torque shafts 240 are connected to the attachment members 138, if the prosthetic valve 100 is in a radially expanded state, the output torque shafts 240 can be rotated (for example, in a clockwise direction) thereby causing the screws 132 to rotate and radially compress the frame 102. Conventional techniques and devices can then be used to insert and advance the delivery apparatus 200 and the prosthetic valve 100 through a patient's vasculature to the desired implantation site. For example, a prosthetic aortic valve can be delivered in a retrograde approach by advancing the delivery apparatus through a femoral artery and the aorta to the native aortic valve.

At or adjacent the implantation site, the handle 210 can be actuated, such as by pressing a button (e.g., button 280a or button 282), flipping a switch, turning a dial, or using an alternative method to turn on the motor 212, to rotate the output torque shafts 240 (for example, in an anti-clockwise direction), thereby causing the screws 132 to rotate and radially expand the frame 102 of the prosthetic valve 100. For example, during retrograde delivery of the prosthetic valve to the aortic position, the delivery apparatus is advanced through the descending aorta, the aortic arch, and the ascending aorta to position the prosthetic valve within the native aortic annulus. The input torque shaft 224 desirably is sized such that it extends through the aortic arch and the gearbox 230 and the output torque shafts 240 are positioned within the ascending aorta when the prosthetic valve is at the desired implantation site. In this manner, deflection and resulting elongation and foreshortening of the output torque shafts 240 can be avoided during valve deployment. As such, all of the output torque shafts 240 can be rotated in a synchronized manner at the same torque for even and predictable expansion of the prosthetic valve.

Advantageously, the prosthetic valve 100 is fully operational (allowing antegrade blood to the flow through the valve in one direction and blocking retrograde blood from flowing through the valve) while it is still connected to the delivery apparatus 200. The physician can therefore test the operation of the prosthetic valve before it is released from the delivery apparatus. If needed, the prosthetic valve 100 can be re-collapsed inside the body by reversing the rotation of the motor 212 (for example, rotating the motor in a clockwise direction), re-positioned, and then re-expanded. Reversing the rotation of the motor 212 can be achieved, for example, by pressing button 280b.

If the physician is still not satisfied with the position and/or operation of the prosthetic valve, it can be re-collapsed and removed from the body. Another advantage provided by the actuators 130 is that the prosthetic valve can be expanded to a final expanded diameter in a range of expanded diameters that provides the best fit for the patient's annulus. In particular embodiments, the actuators 130 are self-locking actuators, meaning that the threads of the screws 132 engaging the threads of the anchors 134 and/or anchors 136 resist pushing or pulling forces acting on the actuators and therefore can retain the expanded diameter of the frame 102 after the prosthetic valve is released from the delivery apparatus. Once the frame 102 is radially expanded to a desired size, the sleeves 270 can be retracted and the output torque shafts can be disengaged from the screws 132. The delivery apparatus 200 can then be removed from the patient.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.). The disclosed embodiments can also be used to implant prostheses in other lumens of the body. Further, in addition to prosthetic valves, the delivery assembly embodiments described herein can be adapted to deliver and implant various other prosthetic devices such as stents and/or other prosthetic repair devices.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A delivery apparatus comprising:
   a handle;

an outer shaft extending distally from the handle;
a gear mechanism arranged distal to the outer shaft;
an input torque shaft extending distally from the handle through the outer shaft and having a distal end portion operatively connected to the gear mechanism; and
a plurality of output torque shafts operatively connected to and extending distally from the gear mechanism, wherein the gear mechanism is configured to transfer rotational motion from the input torque shaft, which has a central rotation axis that is collinear with a central longitudinal axis of the delivery apparatus, to the plurality of output torque shafts, which each have a rotation axis that is radially offset from the central longitudinal axis.

2. The delivery apparatus of claim 1, wherein the distal end portion of the input torque shaft extends axially beyond the outer shaft.

3. The delivery apparatus of claim 1, further comprising a nose cone mounted on a distal end portion of an innermost shaft of the delivery apparatus, the innermost shaft extending coaxially through the input torque shaft and having a proximal end portion coupled to the handle, and wherein the gear mechanism is disposed closer to the nose cone than the handle.

4. The delivery apparatus of claim 1, further comprising a flex shaft extending through the outer shaft and having a proximal end portion connected to the handle and a distal end portion that extends axially beyond the outer shaft into a proximal opening of a gear mechanism housing of the gear mechanism.

5. The delivery apparatus of claim 4, wherein the distal end portion of the input torque shaft extends axially beyond a distal end of the flex shaft and is connected to a drive gear of the gear mechanism.

6. The delivery apparatus of claim 5, wherein the gear mechanism includes a plurality of driven gears connected to the drive gear and wherein each driven gear of the plurality of driven gears is connected to a respective output torque shaft of the plurality of output torque shafts.

7. The delivery apparatus of claim 1, wherein the handle includes an actuator configured to actuate rotation of the input torque shaft and wherein a proximal end portion of the input torque shaft is connected to the actuator.

8. The delivery apparatus of claim 7, wherein the actuator is a motor and wherein actuation of the motor results in rotation of the input torque shaft.

9. The delivery apparatus of claim 1, wherein the input torque shaft extends at least a majority of a length of the delivery apparatus.

10. The delivery apparatus of claim 1, wherein the gear mechanism comprises:
a drive gear operatively connected to and driven by the input torque shaft; and
a plurality of driven gears configured to be driven by the drive gear, wherein each driven gear is operatively coupled to an rotates one of the output torque shafts.

11. The delivery apparatus of claim 10, wherein the drive gear comprises an internal gear and the plurality of driven gears comprise a plurality of pinion gears positioned inside of the internal gear.

12. The delivery apparatus of claim 10, wherein the gear mechanism further comprises:
a gear mechanism housing, wherein the drive gear and the plurality of driven gears are disposed within the gear mechanism housing;
a proximal plate housed within the drive gear;
a distal plate mounted to a distal end of the gear mechanism housing; and
a tubular portion extending from the proximal plate to the distal plate, wherein the plurality of driven gears are disposed around the tubular portion, and wherein the tubular portion defines a lumen for an innermost shaft of the delivery apparatus to extend therethrough.

13. The delivery apparatus of claim 12, wherein the drive gear has teeth than mesh with teeth of each driven gear and wherein a nose cone is mounted on a distal end portion of the innermost shaft.

14. The delivery apparatus of claim 1, wherein the plurality of output torque shafts comprises three output torque shafts and wherein each output torque shaft of the plurality of output torque shafts comprises a connector at its distal end configured to form a releasable connection with an actuator of a mechanically expandable prosthetic heart valve.

15. A delivery assembly comprising:
a prosthetic heart valve comprising a radially expandable and compressible frame and a plurality of actuators configured to radially expand and compress the frame; and
a delivery apparatus comprising:
a handle;
an outer shaft extending distally from the handle;
a gear mechanism arranged distal to the outer shaft;
an input torque shaft extending distally from the handle through the outer shaft and having a distal end portion operatively connected to the gear mechanism; and
a plurality of output torque shafts operatively connected to and extending distally from the gear mechanism, wherein the gear mechanism is configured to transfer rotational motion from the input torque shaft to the plurality of output torque shafts; and
wherein each output torque shaft of the plurality of output torque shafts is releasably coupled to a respective actuator of the plurality of actuators of the prosthetic heart valve such that rotation of the plurality of output torque shafts causes the plurality of actuators to radially expand or compress the prosthetic heart valve.

16. The delivery apparatus of claim 15, wherein the input torque shaft has a central rotation axis that is collinear with a central longitudinal axis of the delivery apparatus and the plurality of output torque shafts each have a rotation axis that is radially offset from the central longitudinal axis.

17. The delivery apparatus of claim 15, wherein the delivery apparatus further comprises:
an innermost shaft that extends coaxially through the input torque shaft and has a proximal end portion coupled to the handle; and
a nose cone mounted on a distal end portion of the innermost shaft, wherein the gear mechanism is disposed closer to the nose cone than the handle and wherein the prosthetic heart valve is coupled to a distal end of the delivery apparatus, adjacent to the nose cone.

18. A method comprising:
inserting a prosthetic heart valve and a distal end portion of a delivery apparatus into a patient's vasculature, wherein the prosthetic heart valve is in a radially compressed state on the distal end portion and the delivery apparatus comprises:
a handle;
an outer shaft extending distally from the handle;
a gear mechanism arranged distal to the outer shaft and inserted into the patient's vasculature;

an input torque shaft extending distally from the handle through the outer shaft and having a distal end portion operatively coupled to the gear mechanism; and a plurality of output torque shafts operatively coupled to the gear mechanism, each output torque shaft having a proximal end portion coupled to the gear mechanism and a distal end portion releasably coupled to a respective actuator of a plurality of actuators on the prosthetic heart valve; and rotating the input torque shaft, which produces rotation of the plurality of output torque shafts via the gear mechanism, wherein the rotation of the plurality of output torque shafts actuates the plurality of actuators, which cause the prosthetic heart valve to expand from the radially compressed state to a radially expanded state.

19. The method of claim 18, wherein each of the plurality of output torque shafts are rotated at a different rotational speed than the input torque shaft.

20. The method of claim 18, wherein rotating the input torque shaft includes rotating the input torque shaft around a central rotation axis that is collinear with a central longitudinal axis of the delivery apparatus and rotating the plurality of output torque shafts around rotation axes that are radially offset from the central longitudinal axis.

* * * * *